United States Patent [19]
Nelson

[11] 3,980,692
[45] Sept. 14, 1976

[54] 5-OXA-17,18-DEHYDROPROSTAGLANDIN-$E_1$-TYPE ANALOGS

[75] Inventor: Norman A. Nelson, Galesburg, Mich.

[73] Assignee: The Upjohn Company, Kalamazoo, Mich.

[22] Filed: Dec. 6, 1974

[21] Appl. No.: 530,230

Related U.S. Application Data

[62] Division of Ser. No. 361,991, May 21, 1973, Pat. No. 3,931,279.

[52] U.S. Cl. .................. 260/468 D; 260/501.1; 260/514 D
[51] Int. Cl.² .................. C07C 61/38; C07C 69/74; C07C 177/00

[58] Field of Search ............... 260/468 D, 514 D

[56] References Cited
UNITED STATES PATENTS
3,923,862   12/1975   Nelson ............... 260/468

FOREIGN PATENTS OR APPLICATIONS
2,036,471   2/1971   Germany ............... 260/468

*Primary Examiner*—Robert Gerstl
*Attorney, Agent, or Firm*—Morris L. Nielsen

[57]   ABSTRACT

5-Oxa-prostaglandin-type compounds and processes for making them. These compounds are useful for a variety of pharmacological purposes, including antiulcer, inhibition of platelet aggregation, increase of nasal patency, and labor inducement at term.

10 Claims, No Drawings

5-OXA-17,18-DEHYDROPROSTAGLANDIN-E$_1$-TYPE ANALOGS

CROSS REFERENCE TO RELATED APPLICATIONS

This application is a divisional of my co-pending application Ser. No. 361,991 filed May 21, 1973 now U.S. Pat. No. 3,931,279.

BACKGROUND OF THE INVENTION

This invention relates to novel compositions of matter, to novel methods for producing those, and to novel chemical intermediates useful in those processes. Particularly, this invention relates to certain novel analogs of prostaglandins E$_1$, F$_1\alpha$, F$_1\beta$, A$_1$, and B$_1$ in which the C-5 methylene (—CH$_2$) in the prostanoic acid structure is replaced by oxygen (—O—).

The essential material for this application, including the background of the invention, the disclosure of the invention, and the description of the preferred embodiments, including Preparations and Examples, is incorporated by reference from U.S. Pat. No. 3,931,279, columns 1–67 and 73–86, inclusive, under the provisions of M.P.E.P. 608.01(p).

I claim:
1. An optically active compound of the formula

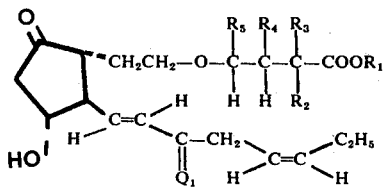

or a racemic compound of that formula and the mirror image thereof, wherein Q$_1$ is

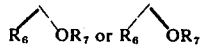

wherein R$_6$ and R$_7$ are hydrogen or alkyl of one to 4 carbon atoms, inclusive, being the same or different; wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein R$_3$ is hydrogen, alkyl of one to 4 carbon atoms, inclusive, or fluoro; wherein R$_2$ is hydrogen or fluoro, with the proviso that R$_2$ is fluoro only when R$_3$ is hydrogen or fluoro; and wherein R$_4$ and R$_5$ are hydrogen or alkyl of one to 4 carbon atoms, inclusive, being the same or different, with the proviso that no more than one of R$_3$, R$_4$, and R$_5$ is alkyl; including the lower alkanoates thereof, and the pharmacologically acceptable salts thereof when R$_1$ is hydrogen.

2. A compound according to claim 1 wherein Q$_1$ is

wherein R$_6$ and R$_7$ are hydrogen or alkyl of one to 4 carbon atoms, inclusive, being the same or different.

3. A compound according to claim 2 wherein the sum of the carbon atoms in R$_6$, R$_7$, R$_8$, and R$_9$ taken together is not greater than 7.

4. A compound according to claim 3 wherein R$_3$, R$_4$, and R$_5$ are either hydrogen or methyl, and one of R$_3$, R$_4$, and R$_5$ is methyl.

5. A compound according to claim 3 wherein R$_2$, R$_3$, R$_4$, and R$_5$ are hydrogen.

6. A compound according to claim 5 wherein R$_6$, R$_7$, R$_8$, and R$_9$ are either hydrogen or methyl, and at least one of R$_6$, R$_7$, R$_8$, and R$_9$ is methyl.

7. A compound according to claim 5 wherein R$_6$, R$_7$, R$_8$, and R$_9$ are hydrogen.

8. A compound according to claim 7 wherein C$_g$H$_{2g}$ is trimethylene.

9. 5-Oxa-17,18-dehydro-PGE$_1$, methyl ester, a compound according to claim 8.

10. A compound according to claim 8 wherein R$_1$ is hydrogen.

* * * * *